United States Patent [19]

Norris

[11] Patent Number: 4,891,210

[45] Date of Patent: Jan. 2, 1990

[54] USE OF BACTERIOPHAGES IN DENTAL HYGIENE

[76] Inventor: Alan H. Norris, 120 Saddle Mountain Rd., Rome, Ga. 30161

[21] Appl. No.: 292,960

[22] Filed: Jan. 3, 1989

[51] Int. Cl.$^4$ .......................... A61K 7/16; A61K 9/68; A61K 39/02
[52] U.S. Cl. ......................................... 424/50; 424/48; 424/49; 424/92; 424/440; 424/441; 132/321
[58] Field of Search ..................... 424/50, 92, 48, 49, 424/440, 441

[56] References Cited

U.S. PATENT DOCUMENTS

| | | | |
|---|---|---|---|
| 2,027,374 | 1/1936 | Fowler | 424/50 |
| 2,944,941 | 7/1960 | Goldenberg | 424/50 |
| 4,133,875 | 1/1979 | Hillman | 424/50 |
| 4,337,314 | 6/1982 | Oeschger et al. | 424/92 |
| 4,454,109 | 6/1984 | Hillman | 424/50 |
| 4,659,561 | 4/1987 | Fives-Taylor et al. | 424/50 |
| 4,681,762 | 7/1987 | Oeschger et al. | 424/92 |
| 4,693,888 | 9/1987 | Miyahara et al. | 424/50 |
| 4,746,512 | 5/1988 | Kawai et al. | 424/50 |
| 4,837,151 | 6/1989 | Stocker | 424/92 |

Primary Examiner—Shep K. Rose

[57] ABSTRACT

Acid forming bacteria in the mouth are controlled by the use of bacteriophages so reducing acid which can cause dental caries.

8 Claims, No Drawings

USE OF BACTERIOPHAGES IN DENTAL HYGIENE

BRIEF SUMMARY OF THE INVENTION

Lactobacilleae are bacteria which act on carbohydrates producing as end products organic acid. In interdental spaces food debris accumulates, bacteria (plaque) are present, decompose the food, and multiply, some bacteria producing acid concentrations which can damage tooth enamel, resulting in dental caries. All bacteria have predatory phages which destroy them. The introduction into the mouth of the Lactobacillus acidophilis phage would quickly reduce the number of such bacteria and so reduce formation of acid. Such phages may be produced from cultures of the host bacteria, isolated and dried to a non active but regeneratable form. This may then be used to introduce the phage to the mouth in regular dosage resulting in much reduced levels of the acid producing varieties of bacteria. Several phages may be required as they are specific to one strain of bacteria. The phages multiply very quickly and one phage can have multiplied 300 times in less than one hour.

BACKGROUND INFORMATION

The published scientific information, for example, as in Zinsser's textbook of Bacteriology, reports Lacto bacillus acidophilus produces no infection in man through some investigators believe that it is of importance in the production of dental caries. Carious lesions of the teeth invariably contain lactic acid producing bacteria.

It is believed that food is trapped in interdental spaces from which it is difficult to remove it. Bacteria of all kinds are in the mouth at all times and these are deposited on these food debris pockets. Some of the bacteria are the lactic acid producing type. Since the food pocket is protected from saliva by its outside layers and the bacteria are anaerobic, acid is produced without dilution in proximity to the tooth surface. This acid can have a concentration which, over time, damages the protective tooth enamel. Once the enamel is penetrated further tooth damage occurs quickly by the acid and by other bacteria.

Brushing and flossing of teeth clean out the food and, if done well, will prevent or retard dental caries. Some toothpastes contain alkali to neutralise the acid. There is a recently developed chewing gum with acid neutralising constituents. All these things help to prevent tooth decay. Their success seems to indicate that the theory of dental caries production is correct as detailed above.

It seems probable that the initial damage to the teeth is caused solely by the acid producers and that the other bacteria are harmless until tooth enamel damage occurs.

A bacteriophage is a minute organism which is a virus. Each virus attacks specific bacteria and there are as many viruses (phages) as there are kinds of bacteria. The virus attaches itself to a bacteria cell and injects its own DNA into the bacteria. This replicates, using the proteins of the bacteria and, at a later stage, the bacteria cell bursts releasing many new phages which then attack other bacteria. Each kind of phage attacks only one kind of bacteria. In the case of the $T_2$ bacterophage acting on a bacteria E. coli the above takes about 30 minutes after exposure of the bacteria to the virus and about 120 phage particles are freed for each bacteria cell attacked. The rapid growth in numbers of phages would obviously reduce the bacteria present in a small localised area to a small number in a matter of a few hours.

Bacteriophages are easily propagated in suitable cultures of the host organism. Studies of the $T_2$ phage on E Coli showed that when the $T_2$ phage was innoculated in liquid cultures in the ratio of 1 phage per 500 bacteria complete lysis (bursting of cells) occured in 8 hours. Using the $T_7$ phage complete lysis occured in 2 hours. Titers indicated 10,000,000,000 phages per ml of liquid. The mass of phage recoverable from such purified preparations is about 5 to 15 milligrams per liter of culture. Hence the method of obtaining phages is well known and completely practical. Phages for prevention of clostridia in silage preparation have been made and sold commercially. The manufacturing methods are available in the prior art.

DESCRIPTION OF THE INVENTION

The strains of acid forming bacteria present in plaque on human teeth are isolated and exposed in cultures. The presence of phages will be shown by changes in the culture solution. Phages will appear as, for example, fruit juice exposed to air will pick up yeast spores and ferment. The phages are isolated, cultivated, and produced in quantity. They are then incorporated in dental care products.

For example, dental floss could be impregnated with a solution containing the mixture of phages and dried at low temperatures. The phages will reactivate when they are rewet. The use of such dental floss would deposit phages into the interdental spaces and prevent any accumulation of acid forming bacteria there. Thus little or no acid is produced to initiate dental caries in these spaces.

For example, the phages could be incorporated in small tablets of sweet pleasantly flavoured substrate. These tablets are used daily, or after meals. They are placed in the mouth and the saliva formed is swished around the teeth. The saliva can be swallowed as the phages are harmless to all other cells than their specific bacterial hosts—in this case, strains of lacto acidophilis.

For example the phages could be incorporated in chewing gum.

For example, the phages could be incorporated in tooth powder and toothpaste.

Regular use of materials containing phages would reduce the acid forming bacteria to a very low level. It would only require that one phage reached each interdental space and contacted one bacteria in that space for the whole space to be cleared of those bacteria in a few hours. It is probable that once phages, which are non mobile, reach each interdental space that they, or their decendants, would persist in that location for some time. And, during a meal which filled the interdental apace with food, they would be trapped inside the food debris, thus providing some extended protection against acid production by L acidophilis or similar strains.

The phages can be swallowed without any danger since they have no deleterious effect on human cells. Any phages reaching the gut would there attack any L acidophilis bacteria they encountered. This may be disadvantageous in the case of babies on a milk diet but it should be remembered that babies have no teeth, no interdental cavities, and no need for dental care.

It is only children growing their second adult teeth who need protection and children of this age do not require the help of such bacteria to digest food. Phages occur naturally and inevitably all people will have ingested some at some time, without any adverse effects.

What I claim is:

1. A method of improved dental hygiene in which bacteriophages are used to reduce the number of harmful bacteria in the interdental spaces.

2. Claim 1 wherein the phages are incorporated in toothpaste.

3. Claim 1 wherein the phages are incorporated in toothpowder.

4. Claim 1 wherein the phages are incorporated in dental floss.

5. Claim 1 wherein the phages are incorporated in chewing gum.

6. Claim 1 wherein the phages are incorporated in oral tablets.

7. Claim 1 wherein the phages are incorporated in mouthwash solutions.

8. Claim 1 wherein the phages are incorporated in sweets and candy.

* * * * *